United States Patent [19]

Schulz et al.

[11] Patent Number: 4,943,315
[45] Date of Patent: Jul. 24, 1990

[54] AGENTS FOR REDUCING TRANSPIRATION OF PLANTS

[75] Inventors: Guenter Schulz, Ludwigshafen; Juergen Schubert; Hubert Sauter, both of Mannheim; Klaus Grosmann; Johann Jung, both of Limburgerhof, all of Fed. Rep. of Germany

[73] Assignee: BASF Aktiengesellschaft, Ludwigshafen, Fed. Rep. of Germany

[21] Appl. No.: 306,560

[22] Filed: Feb. 6, 1989

[30] Foreign Application Priority Data

Feb. 6, 1988 [DE] Fed. Rep. of Germany ....... 3803667

[51] Int. Cl.$^5$ ..................... A01N 47/30; A01N 31/00; A01N 43/00
[52] U.S. Cl. ...................... 71/120; 71/122; 71/88
[58] Field of Search ............................ 71/88, 122, 120

[56] References Cited

U.S. PATENT DOCUMENTS 4,671,816 6/1967 Blicsener et al. .................. 71/88

FOREIGN PATENT DOCUMENTS 78509 6/1987 European Pat. Off. .............. 71/88
3143721 6/1987 Fed. Rep. of Germany ......... 71/88

OTHER PUBLICATIONS

Borgnu et al. Chem. Abst. vol. 91 (1979) 74319m.
Keffard et al., Chem. Abst. vol. 73 (1970) 129778w.
Bruce et al., Chem. Abst. vol. 65(1966) 1279208.

Primary Examiner—Richard L. Raymond
Assistant Examiner—Eric J. Kraus
Attorney, Agent, or Firm—Oblon, Spivak, McClelland, Maier & Neustadt

[57] ABSTRACT

Agents for reducing transpiration in plants and/or avoiding impairment to plants caused by heat and dry stress, comprising a synergistic mixture containing at least one acetylene compound of the formula I

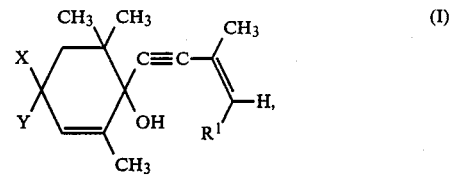

where the substituents have the following meanings
$R^1$ CH$_2$OH, COOH, CH$_2$OR$^4$, COOR$^4$ or CHXY,
OR$^2$ and
Y OR$^3$ or X and Y together are C$_2$–C$_5$-alkylenedioxy which is unsubstituted or mono-, di- or trisubstituted by C$_1$–C$_4$-alkyl, or are a doubly bonded oxygen atom,
$R^2$, $R^3$ C$_1$–C$_8$-alkyl and
$R^4$ C$_1$–C$_8$-alkyl, C$_2$–C$_8$-alkoxyalkyl, C$_2$–C$_4$-haloalkyl, phenyl or C$_7$–C$_{16}$-phenylalkyl, and at least one phenylbenzylurea of the general formula II

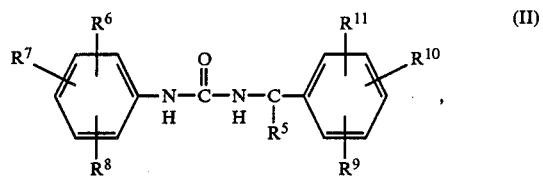

where the substituents have the following meanings
$R^5$ hydrogen, C$_1$–C$_4$-alkyl, C$_1$–C$_4$-alkoxy, C$_1$–C$_4$-haloalkyl, C$_1$–C$_4$-haloalkoxy, phenyl or C$_7$–C$_{16}$-phenylalkyl and
$R^6$–$R^{11}$ hydrogen, C$_1$–C$_4$-alkyl, C$_1$–C$_4$-alkoxy halogen, C$_1$–C$_4$-haloalkyl, C$_1$–C$_4$-haloalkoxy, phenyl, phenoxy, nitro, cyano, hydroxy, OR$^4$, CHO or COOR$^4$.

11 Claims, No Drawings

AGENTS FOR REDUCING TRANSPIRATION OF PLANTS

The present invention relates to agents which are based on acetylene compounds and phenylbenzylureas and are intended for reducing transpiration of plants and/or for avoiding adverse effects on the plants caused by stress due to heat and aridity.

The present invention furthermore relates to a process for reducing transpiration of plants, and the use of a mixture consisting of one or more acetylene compounds and one or more phenylbenzylureas for reducing transpiration in plants.

It is known that the phytohormone abscisic acid (ABA) which occurs naturally in plants regulates various physiological processes in the plants (Die Pharmazie 27.619 (1972); B. V. Milborrow, Abscisic Acid in Phytohormones and Related Compounds—A Comprehensive Treatise, Vol. I, page 295 et seq, Editors: Letham, Goodwin and Higgins, Elsevier 1978).

ABA influences, for example, the dormancy of seed and buds, the ripening of fruit and the abscission process of fruit and leaves. Abscisic acid is particularly important for regulating the water balance of the plant. For example, in the event of aridity, the endogenous concentration of ABA in the leaves is increased by a greater level of biosynthesis; this increased concentration then causes the stomata to close and thus results in less water being released by the plant via the stomata (less stomatal transpiration). This allows the plant to compensate for an inadequate water supply. However, in the case of severe stress, the action of the endogenous ABA is not always sufficient to protect the plant from damage due to heat and aridity.

Exogenously supplied ABA, for example ABA supplied by spraying the plants with solutions of ABA, leads to increased closing of the stomata and hence to considerably reduced transpiration. The plants treated are thus substantially more resistant than untreated plants to stress due to heat and aridity.

Thus, treatment of crop plants with transpiration inhibitors would be of very great benefit in agriculture, since such a treatment makes it possible to avoid damage to crop plants caused by stress which is due to heat and aridity and may lead to an internal lack of water, to wilting, to lower yields and even to death. In some agricultural areas, in particular in arid areas which are regularly threatened by heat and aridity, such damage represents a considerable problem. In such areas, there is an urgent need for agents to reduce transpiration of crop plants.

Although exogenously applied ABA is suitable as a transpiration inhibitor for crop plants owing to its biological action, it has not been used in agriculture to date. The reason for this is that it is impossible for sufficient amounts of ABA to be made available using equipment which is technically sufficiently simple to be acceptable for the particular agricultural aim. ABA occurs only in very small amounts in plants and is very expensive to isolate from plants. On the other hand, the known total syntheses of abscisic acid [J. W. Cornforth et al., J. Chem. Soc. C. (1968), 1565; D. L. Roberts et al., J. Org. Chem. 33 (1968), 3566; T. Oritani et al., Agric. Biol. Chem. (Tokyo) 34 (1970), 108; J. A. Findlay et al., Can. J. Chem. 49 (1971), 2369; H. J. Mayer et al., Helv. Chim. Acta 59 (1976), 1424; F. Kienzle et al., Helv. Chim. Acta 61 (1978), 2616; M. G. Constantino et al., J. Org. Chem. 51 (1986), 253] are so difficult and so expensive and require such complicated apparatus that ABA cannot be considered for the preparation of agents for regulating plant growth, in particular for the preparation of agents for regulating transpiration of crop plants.

It is also known that the ABA-like acetylene compounds disclosed in DE-A No. 31 43 721 and in EP-A No. 78 509, which are of the formula I, correspond to natural ABA in their biological activity (cf. J. Jung and K. Grossmann, J. Plant Physiol. 121 (1985), 361).

We have found that agents which contain one or more acetylene compounds of the general formula I

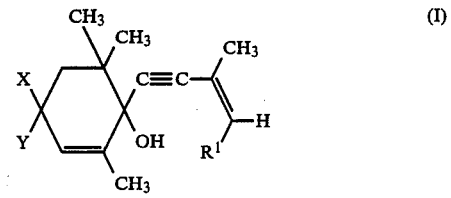

where $R^1$ is $CH_2OH$, $COOH$, $CH_2OR^4$, $COOR^4$ or CHXY, X is $OR^2$ and Y is $OR^3$, or X and Y together are $C_2$-$C_5$-alkylenedioxy which is unsubstituted or mono-, di- or trisubstituted by $C_1$-$C_4$-alkyl or are an oxygen atom having a double bond, $R^2$ and $R^3$ are each $C_1$-$C_8$-alkyl and $R^4$ is $C_1$-$C_8$-alkyl, $C_2$-$C_8$-alkoxyalkyl, $C_2$-$C_4$-haloalkyl, phenyl or $C_7$-$C_{16}$-phenylalkyl, and one or more phenylbenzylureas of the general formula II

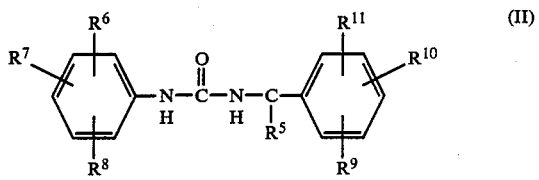

where $R^5$ is hydrogen, $C_1$-$C_4$-alkyl, $C_1$-$C_4$-alkoxy, $C_1$-$C_4$-haloalkyl, $C_1$-$C_4$-haloalkoxy, phenyl or $C_7$-$C_{16}$-phenylalkyl and $R^6$-$R^{11}$ independently of one another are each hydrogen, $C_1$-$C_4$-alkyl, $C_1$-$C_4$-alkoxy, halogen, $C_1$-$C_4$-haloalkyl, $C_1$-$C_4$-haloalkoxy, phenyl, phenoxy, nitro, cyano, hydroxyl, $OR^4$, CHO or $COOR^4$, reduce transpiration of plants and/or avoid adverse effects on the plants due to stress caused by heat and aridity, synergistic effects occurring.

We have furthermore found a process for their application and their use for reducing transpiration of plants.

Some of the acetylene compounds I are disclosed in DE-A No. 31 43 721 and in EP-A No. 78 509; those which are unknown can be prepared by known methods (Liebigs Ann. Chemie, 1979, pages 1945-1951; J. Org. Chem. 51 (1986), 253-254).

The phenylbenzylureas of the formula II are disclosed in, for example, J. Chim. Chem. Soc. 13 (1946), 22, Helv. Chim. Acta 21 (1938), 1137, Can. J. Chem. 30 (1952), 225 and Can. J. Chem. 31 (1953), 896; those which are unknown can be prepared by methods which are known per se (Houben/Weyl, Vol. VIII, page 149 et seq, Georg Thieme Verlag, Stuttgart, 1952).

The substituents in the formulae I and II have the following specific meanings:

$R^1$ is $CH_2OH$, COOH, $CH_2OR^4$, $COOR^4$ or $CH(OR^2)(OR^3)$,

X is $OR^2$,

Y is $OR^3$,

X and Y together are =O, $C_2$–$C_5$-alkylenedioxy, such as O—$(CH_2)_2$—O, O—$(CH_2)_3$O, O—$(CH_2)_4$—O and O—$(CH_2)_5$—O, or $C_2$–$C_5$-alkylenedioxy which is mono-, di- or trisubstituted by $C_1$–$C_4$-alkyl, such as
—CH(CH$_3$)CH$_2$—, —CH(C$_2$H$_5$)CH$_2$—, —CH(CH$_3$)CH(CH$_3$)—, —CH(CH$_3$)CH$_2$CH$_2$—, —CH$_2$CH(CH$_3$)—CH$_2$—, —CH$_2$C(CH$_3$)$_2$CH$_2$—, —CH(CH$_3$)CH$_2$CH(CH$_3$)—, —CH(CH$_3$)CH$_2$CH$_2$CH$_2$—, —CH$_2$CH(CH$_3$)CH$_2$CH$_2$—, —CH$_2$—CH(CH$_3$)CH(CH$_3$)CH$_2$—, —CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$— and —CH$_2$CH$_2$CH(CH$_3$)CH$_2$CH$_2$—, $R^2$ and $R^3$ are each $C_1$–$C_8$-alkyl, preferably $C_1$–$C_4$-alkyl, such as methyl, ethyl, n-propyl, isopropyl, n-butyl, isobutyl, sec-butyl or tert-butyl, $R^4$ is $C_1$–$C_8$-alkyl, preferably $C_1$–$C_4$-alkyl, such as methyl, ethyl, n-propyl, isopropyl, n-butyl, isobutyl, sec-butyl or tert-butyl, $C_2$–$C_8$-alkoxyalkyl, preferably $C_2$–$C_4$-alkoxyalkyl, such as methoxymethyl, methoxyethyl, methoxy-n-propyl, methoxyisopropyl, ethoxymethyl, ethoxyethyl, n-propoxymethyl and isopropoxymethyl, $C_1$–$C_4$-haloalkyl, preferably $C_1$–$C_4$-fluoro- and/or chloroalkyl, particularly preferably $C_1$- or $C_2$-fluoro- and/or chloroalkyl, such as fluoromethyl, difluoromethyl, trifluoromethyl, chloromethyl, dichloromethyl, trichloromethyl, chlorofluoromethyl, dichlorofluoromethyl, chlorodifluoromethyl, 2,2,2-trifluoroethyl, 2,2,2-trichloroethyl, pentafluoroethyl or pentachloroethyl, phenyl, and $C_7$–$C_{16}$-phenylalkyl, preferably $C_7$–$C_{10}$-phenylalkyl, such as benzyl, 1-phenethyl or 2-phenethyl, $R^5$ is hydrogen, $C_1$–$C_4$-alkyl, such as methyl, ethyl, n-propyl, isopropyl, n-butyl, sec-butyl or tert-butyl, preferably methyl or ethyl, $C_1$–$C_4$-alkoxy, such as methoxy, ethoxy, n-propoxy, isopropoxy, n-butoxy, isobutoxy, sec-butoxy or tert-butoxy, preferably methoxy or ethoxy, $C_1$–$C_4$-haloalkoxy, preferably $C_1$–$C_4$-fluoro- and/or chloroalkyl, particularly preferably $C_1$- or $C_2$-fluoro and/or chloroalkyl, such as fluoromethyl, difluoromethyl, trifluoromethyl, chloromethyl, dichloromethyl, trichloromethyl, chlorofluoromethyl, dichlorofluoromethyl, chlorodifluoromethyl, 2,2,2-trifluoromethyl, 2,2,2-trichloroethyl, pentafluoroethyl or pentachloroethyl, $C_1$–$C_4$-haloalkoxy, preferably $C_1$–$C_4$-fluoro- and/or chloroalkoxy, particularly preferably $C_1$- or $C_2$-fluoro- and/or chloroalkoxy, such as fluoromethoxy, difluoromethoxy, trifluoromethoxy, chloromethoxy, dichloromethoxy, trichloromethoxy, chlorofluoromethoxy, dichlorofluoromethoxy, chlorodifluoromethoxy, 2,2,2-trifluoroethoxy, 2,2,2-trichloroethoxy, pentafluoroethoxy or pentachloroethoxy, phenyl, or $C_7$–$C_{16}$-phenylalkyl, preferably $C_7$–$C_{10}$-phenylalkyl, such as benzyl, 1-phenethyl or 2-phenethyl, and $R^6$–$R^{11}$ independently of one another are each hydrogen, $C_1$–$C_4$-alkyl, such as methyl, ethyl, n-propyl, isopropyl, n-butyl, isobutyl, sec-butyl or tert-butyl, preferably methyl or ethyl, $C_1$–$C_4$-alkoxy, such as methoxy, ethoxy, n-propoxy, isopropoxy, n-butoxy, isobutoxy, sec-butoxy or tert-butoxy, preferably methoxy or ethoxy, halogen, such as fluorine, chlorine, bromine or iodine, preferably fluorine, chlorine or bromine, $C_1$–$C_4$-haloalkyl, preferably $C_1$–$C_4$-fluoro- and/or chloroalkyl, particularly preferably $C_1$- or $C_2$-fluoro- and/or chloroalkyl, such as fluoromethyl, difluoromethyl, trifluoromethyl, chloromethyl, dichloromethyl, trichloromethyl, chlorofluoromethyl, dichlorofluoromethyl, chlorodifluoromethyl, 2,2,2-trifluoroethyl, 2,2,2-trichloroethyl, pentafluoroethyl or pentachloroethyl, $C_1$–$C_4$-haloalkoxy, preferably $C_1$–$C_4$-fluoro-and/or chloroalkoxy, particularly preferably $C_1$- or $C_2$-fluoro-and/or chloroalkoxy, such as fluoromethoxy, difluoromethoxy, trifluoromethoxy, chloromethoxy, dichloromethoxy, trichloromethoxy, chlorofluoromethoxy, dichlorofluoromethoxy, chlorodifluoromethoxy, 2,2,2-trifluoroethoxy, 2,2,2-trichloroethoxy, 1,1,2,2-tetrafluoroethoxy, pentafluoroethoxy or pentachloroethoxy, halogen, preferably fluorine, chlorine or bromine, phenyl, phenoxy, nitro, cyano, hydroxyl, $OR^4$, CHO or $COOR^4$.

The compounds I and II are present in the novel agents in weight ratios of from 10:1 to 0.01:1, preferably from 5:1 to 0.05:1, particularly preferably from 2:1 to 0.2:1.

The acetylene compounds I can be applied at rates of from 0.01 to 10, preferably from 0.1 to 3, kg/ha, and the ureas II can be applied at rates of from 0.05 to 10, preferably from 0.1 to 3, kg/ha.

The agents according to the invention may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the agents, or active ingredients contained therein, as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions, water-dispersible granules or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The agents according to the invention are applied by spraying or dusting the plants and/or the soil with the agents, or treating the seeds of the plants with the agents.

In view of the spectrum of action and the desired influence on transpiration behavior in plants, and in view of the numerous application methods possible, the agents according to the invention may, depending on the substitution pattern, be used in a large number of plants.

The following plants are suitable:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Elais guineensis | oil palms |
| Fragaria vesca | strawberries |
| Glycine max | soybeans |
| Gossypium hirsutum (Gossypium arboreum, Gossypium herbaceum, Gossypium vitifolium | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa lucerne |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (S. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To broaden the spectrum of action and to achieve additional effects, the agents according to the invention may be mixed with each other and with representatives of herbicidal, growth-regulating or fungicidal active ingredients.

It may also be useful to apply the agents according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The formulations or the ready-to-use forms prepared therefrom, such as solutions, emulsions, suspensions, powders, dusts, pastes or granules, are applied in conventional manner, for example preemergence, postemergence, or as seed dressings.

Examples of formulations are given below:

I. 20 parts by weight of a mixture of I/1 and II/1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of a mixture of I/1 snd II/2 is intimately mixed with 97 parts by weight of particulate kaolin. A dust is obtained containing 3% by weight of the active ingredient.

III. 30 parts by weight of a mixture of I/1 and II/3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV a mixture of I/1 and II/4 by weight of comnd II/4 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt % of active ingredient.

V. 20 parts of a mixture of I/1 and II/5 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of a mixture of I/1 and II/6 is mixed with 10 parts by weight of N-methyl-alpha-pyrrolidone. A mixture is obtained which is suitable for application in the form of very fine drops.

VII. 20 parts by weight of a mixture of I/1 and II/1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VIII. 20 parts by weight of a mixture of I/1 and II/1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02 by weight of the active ingredient.

IX. 20 parts by weight of a mixture of I/1 and II/1 is dissolved in a mixture consisting of 25 parts by weight of cyclohexanol, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

Examples of compounds I and II which the agents according to the invention may contain are given in the following table:

TABLE 1

(I) — structure with cyclohexene ring bearing X, Y substituents, gem-dimethyl, CH$_3$, OH, C≡C-C(CH$_3$)=CH-R$^1$

| Compound No. | R$^1$ | X | Y |
|---|---|---|---|
| I/1 | —CH(OCH$_3$)$_2$ | | O—CH(CH$_3$)CH$_2$—O |
| I/2 | (dioxolane: O-CH$_2$-CH$_2$-O spiro) | | O—CH(CH$_3$)CH$_2$—O |
| I/3 | (dioxolane with CH$_3$) | | O—CH(CH$_3$)CH$_2$—O |
| I/4 | —CH(OCH$_3$)$_2$ | | O—CH$_2$CH$_2$—O |
| I/5 | (dioxolane spiro) | | O—CH$_2$CH$_2$—O |
| I/6 | (dioxolane with CH$_3$) | | O—CH$_2$CH$_2$—O |
| I/7 | —CHO | | O—CH$_2$CH$_2$—O |
| I/8 | —CH$_2$OH | | O—CH$_2$CH$_2$—O |
| I/9 | —CH$_{2L}$ $_{OCH3}$ | | O—CH$_2$CH$_2$—O |
| I/10 | —CH$_2$OCH$_2$OCH$_3$ | | O—CH$_2$CH$_2$—O |
| I/11 | —COOH | | O—CH$_2$CH$_2$—O |
| I/12 | —COOCH$_3$ | | O—CH$_2$CH$_2$—O |
| I/13 | —COOC$_2$H$_5$ | | O—CH$_2$CH$_2$—O |
| I/14 | —CH$_2$OH | | O—CH$_2$C(CH$_3$)$_2$CH$_2$—O |
| I/15 | —CHO | | O—CH$_2$C(CH$_3$)$_2$CH$_2$—O |
| I/16 | (dioxolane spiro) | | O—CH$_2$C(CH$_3$)$_2$CH$_2$—O |
| I/17 | —CH(OCH$_3$)$_2$ | | O—CH$_2$C(CH$_3$)$_2$CH$_2$—O |
| I/18 | —COOH | | O—CH$_2$C(CH$_3$)$_2$CH$_2$—O |
| I/19 | —COOCH$_3$ | | O—CH$_2$C(CH$_3$)$_2$CH$_2$—O |
| I/20 | —CH$_2$OH | | =O |
| I/21 | —CH$_2$OCH$_3$ | | =O |
| I/22 | —CH$_2$OCH$_2$OCH$_3$ | | =O |
| I/23 | —CHO | | =O |
| I/24 | (dioxolane spiro) | | =O |
| I/25 | —CH(OCH$_3$)$_2$ | | =O |
| I/26 | —COOH | | =O |

TABLE 1-continued (I) Structure: cyclohexene with CH3 groups, C≡C-C(CH3)=CH-R¹, OH, X, Y substituents

| Compound No. | R¹ | X | Y |
|---|---|---|---|
| I/27 | —COOCH₃ | =O | |
| I/28 | —COOC₂H₅ | =O | |
| I/29 | —CH(OCH₃) | OCH₃ | OCH₃ |
| I/30 | —COOCH₃ | OCH₃ | OCH₃ |

TABLE 2

(II) Structure: R⁶,R⁷,R⁸-substituted phenyl—NH—C(=O)—N(H)—C(R⁵)—phenyl with R⁹,R¹⁰,R¹¹

| Compound No. | R⁵ | R⁶ | R⁷ | R⁸ | R⁹ | R¹⁰ | R¹¹ |
|---|---|---|---|---|---|---|---|
| II/1 | H | H | H | H | H | H | H |
| II/2 | H | 4-fluoro | H | H | H | H | H |
| II/3 | H | 4-chloro | H | H | H | H | H |
| II/4 | H | 4-bromo | H | H | H | H | H |
| II/5 | H | 2-chloro | H | H | H | H | H |
| II/6 | H | 2-methyl | H | H | H | H | H |
| II/7 | H | 4-methyl | H | H | H | H | H |
| II/8 | H | 4-nitro | H | H | H | H | H |
| II/9 | H | 4-cyano | H | H | H | H | H |
| II/10 | H | 4-CHO | H | H | H | H | H |
| II/11 | H | 4-COOCH₃ | H | H | H | H | H |
| II/12 | H | 4-O-phenyl | H | H | H | H | H |
| II/13 | H | 4-OH | H | H | H | H | H |
| II/14 | H | 4-OCH₃ | H | H | H | H | H |
| II/15 | H | 4-CF₃ | H | H | H | H | H |
| II/16 | C₂H₅ | H | | | | | |
| II/17 | CH₃ | H | | | | | |
| II/18 | CH₃ | 4-fluoro | H | H | H | H | H |
| II/19 | CH₃ | 4-chloro | H | H | H | H | H |
| II/20 | CH₃ | 4-bromo | H | H | H | H | H |
| II/21 | CH₃ | 4-CH₃ | 2-CH₃ | 6-CH₃ | H | H | H |
| II/22 | CH₃ | 2-CH₃ | H | H | H | H | H |
| II/23 | CH₃ | 2-chloro | H | H | H | H | H |
| II/24 | H | H | H | H | 4-CH₃ | H | H |
| II/25 | H | 4-CH₃ | H | H | 4-CH₃ | H | H |
| II/26 | H | 4-fluoro | H | H | 2-CH₃ | 4-CH₃ | 6-CH₃ |
| II/27 | H | 4-fluoro | H | H | 4-chlor | H | H |
| II/28 | CH₃ | 4-CH₃ | H | H | 4-CH₃ | H | H |
| II/29 | CH₃ | 4-fluoro | H | H | 4-CH₃ | H | H |

USE EXAMPLES

Examples A to C

Spring barley (Hordeum vulgare L. cv. Union) was grown for 14 days under standardized greenhouse conditions in a peat substrate (80 plants/500 ml pot) (Jung and Grossmann, J. Plant Physiol., 121, 361–367, 1985). The plants were watered adequately and the foliage was treated with aqueous formulations of the agents given in Tables A and B. The water consumed by the plants was determined by weighing the pots on certain days and adding the amount of water consumed. The agents were prepared from compounds I and II, formulated in a mixture of cyclohexanone (4 parts) and Emulphor EL (1 part). The final amount of formulating agent in the aqueous formulation of the agents was approx. 2 vol %. The amount of spray liquor applied was equivalent to 1,000 liters/ha.

TABLE A

| Compound No. | Amount of compound, or mixture of compounds, applied [kg/ha] | Water consumption % day 2nd | 4th | 7th | as a percentage of overall consumption (= control) |
|---|---|---|---|---|---|
| I/1 | 0.25 | 80 | 103 | 97 | 94 |
| I/1 | 0.5 | 72 | 95 | 95 | 87 |
| II/1 | 2.0 | 97 | 96 | 100 | 97 |
| I/1 + II/1 | 0.25 + 2.0 | 61 | 83 | 90 | 78 |
| I/1 +0 II/1 | 0.5 + 2.0 | 59 | 76 | 84 | 73 |
| untreated (control) | 0 | 100 | 100 | 100 | 100 |

TABLE B

| Compound No. | Amount of compound, or mixture of compounds, applied [kg/ha] | Water consuption % day 1st | 4th | 7th | 11th | as a percentage of overall consumption |
|---|---|---|---|---|---|---|
| I/1 | 1 | 49 | 74 | 85 | 90 | 79 |
| I/1 + II/1 | 1 + 2 | 43 | 58 | 65 | 76 | 64 |
| untreated | 0 | 100 | 100 | 100 | 100 | 100 |

The results presented in Tables A and B show that II/1 on its own has no influence on the water consumption of the plants. However, when II/1 is combined with I/1, which reduces plant transpiration, the action of I/1 is significantly increased. The water consumption is restricted more efficiently and for a longer period of time, as a result of which the plant is able to handle its water reserves more economically. When the water supply is stopped completely, wilting, senescence and drying-out phenomena occur a few days later than in the plants treated just with I/1.

Example C

Spring barley was cultivated under greenhouse conditions and treated as described in Examples A and B. The water consumption of the plants was determined on certain days by weighing.

TABLE C

| Compound No. | Amount of compound, or mixture of compounds, applied [kg/ha] | Water consumption in % day 2nd | 4th | 7th | as a percentage of overall consumption (control) |
|---|---|---|---|---|---|
| I/5 | 0.25 | 63 | 76 | 100 | 80 |
| I/5 | 0.5 | 62 | 73 | 99 | 76 |
| I/5 | 1.0 | 57 | 54 | 84 | 62 |
| I/5 + II/1 | 0.25 + 2.0 | 57 | 58 | 92 | 66 |
| I/5 + II/1 | 0.5 + 2.0 | 53 | 47 | 74 | 54 |
| I/5 + II/1 | 1.0 + 2.0 | 53 | 43 | 69 | 51 |
| untreated (control) | 0 | 100 | 100 | 100 | 100 |
| I/3 | 0.25 | 67 | 78 | 99 | 81 |
| I/3 | 0.5 | 69 | 78 | 100 | 81 |
| I/3 | 1.0 | 59 | 56 | 81 | 62 |
| I/3 + II/1 | 0.25 + 2.0 | 58 | 65 | 94 | 69 |
| I/3 + II/1 | 0.5 + 2.0 | 55 | 58 | 87 | 65 |
| I/3 + II/1 | 1.0 + 2.0 | 54 | 48 | 71 | 56 |
| untreated (control) | 0 | 100 | 100 | 100 | 100 |

Table C shows that II/1 in combination with I/5 and I/3 significantly increases their antitranspirant action.

Example D

Spring barley was cultivated under greenhouse conditions and treated as described in Example A. The water consumption was determined 11 days after the treatment by weighing.

TABLE D

| Compound No. | Amounts of Compound, or mixture of compounds, applied [kg/ha] | Water consumption in % 11 days after treatment |
|---|---|---|
| I/1 | 1 | 84 |
| II/1 | 2 | 97 |
| II/2 | 2 | 100 |
| II/3 | 2 | 99 |
| II/4 | 2 | 98 |
| II/5 | 2 | 99 |
| II/6 | 2 | 102 |
| I/1 + II/1 | 1 + 2 | 69 |
| I/1 + II/2 | 1 + 2 | 68 |
| I/1 + II/3 | 1 + 2 | 74 |
| I/1 + II/4 | 1 + 2 | 72 |
| I/1 + II/5 | 1 + 2 | 75 |
| I/1 + II/6 | 1 + 2 | 78 |

TABLE D-continued

| Compound No. | Amounts of Compound, or mixture of compounds, applied [kg/ha] | Water consumption in % 11 days after treatment |
|---|---|---|
| Untreated (control) | 0 | 100 |

Table D shows that the ureas II/1 to II/6 synergistically increase the antitranspirant action of I/1.

We claim:

1. An agent for reducing transpiration in plants and for avoiding impairment to plants caused by heat and dry stress, comprising a synergistic mixture of at least one acetylene compound of the general formula I

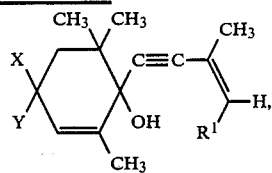

(I)

where the substituents have the following meanings
$R_1$ is $CH(OR^2)(OR^3)$ or CHXY,
wherein X and Y together are $C_2$- or $C_3$-alkylenedioxy which is unsubstituted or mono- or disubstituted by methyl or ethyl,
$R^2$, $R^3$ is $C_1$-$C_4$-alkyl
and at least one phenylbenzylurea of the general formula II

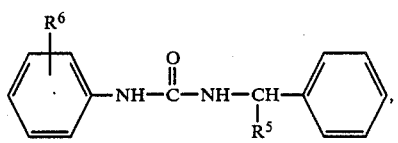

(II)

where the substituents have the following meanings

R[5] is hydrogen or methyl and R[6] is hydrogen, methyl or halogen, wherein an excess of compound II is employed.

2. An agent as set forth in claim 1, wherein compounds I and II are in a weight ratio of from about 0.01:1 to 1:1.

3. An agent as set forth in claim 1, containing from 0.1 to 95 wt % of a synergistic mixture of an acetylene compound I and a phenylbenzylurea II, and conventional inert additives.

4. A process for reducing transpiration in plants, wherein the plants, the seed or the soil are treated with an effective amount for reducing transpiration in plants of an agent as set forth in claim 1.

5. An agent as set forth in claim 1, wherein R[1] is —CH(OCH$_3$)$_2$ and X and Y together are O—CH(CH$_3$)CH$_2$—O.

6. An agent as set forth in claim 1, wherein R[1] is

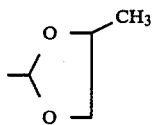

and X and Y together are O—CH(CH$_3$)CH$_2$—O.

7. An agent as set forth in claim 1, wherein R[1] is

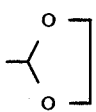

and X and Y together are O—CH$_2$CH$_2$—O.

8. An agent for reducing transpiration in plants and for avoiding impairment to plants caused by heat and dry stress, comprising a synergistic mixture of at least one acetylene compound of the general formula I

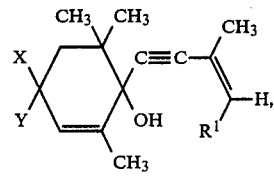

where the substituents have the following meanings
R[1] is COOH or COOR[4]
X and Y together are C$_2$- or C$_3$-alkylenedioxy which is unsubstituted or mono- or disubstituted by methyl or ethyl, or are a doubly bonded oxygen atom,
R[4] is C$_1$-C$_4$-alkyl
and at least one phenylbenzylurea of the general formula II

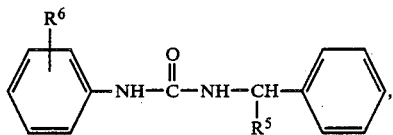

where the substituents have the following meanings
R[5] is hydrogen or methyl and
R[6] is hydrogen, methyl or halogen, wherein an excess of compound II is employed.

9. An agent as set forth in claim 8, wherein compounds I and II are in a weight ratio of from about 0.01:1 to 1:1.

10. An agent as set forth in claim 8 containing from 0.1 to 95 wt. % of a synergistic mixture of an acetylene compound I and a phenylbenzylurea II, and conventional inert additives.

11. A process for reducing transpiration in plants, wherein the plants, the seed or the soil are treated with an effective amount for reducing transpiration in plants of an agent as set forth in claim 8.

* * * * *

UNITED STATES PATENT AND TRADEMARK OFFICE
CERTIFICATE OF CORRECTION

PATENT NO. : 4,943,315

DATED : JULY 24, 1990

INVENTOR(S) : GUENTER SCHULZ, ET AL.

It is certified that error appears in the above-identified patent and that said Letters Patent is hereby corrected as shown below:

Title page:

In the inventors, delete "Grosmann" and insert --Grossmann--.

Signed and Sealed this

Twenty-eighth Day of January, 1992

Attest:

HARRY F. MANBECK, JR.

Attesting Officer   Commissioner of Patents and Trademarks